Nov. 19, 1963
R. M. MANCE
APPLE TREE
Filed March 19, 1962
Plant Pat. 2,313
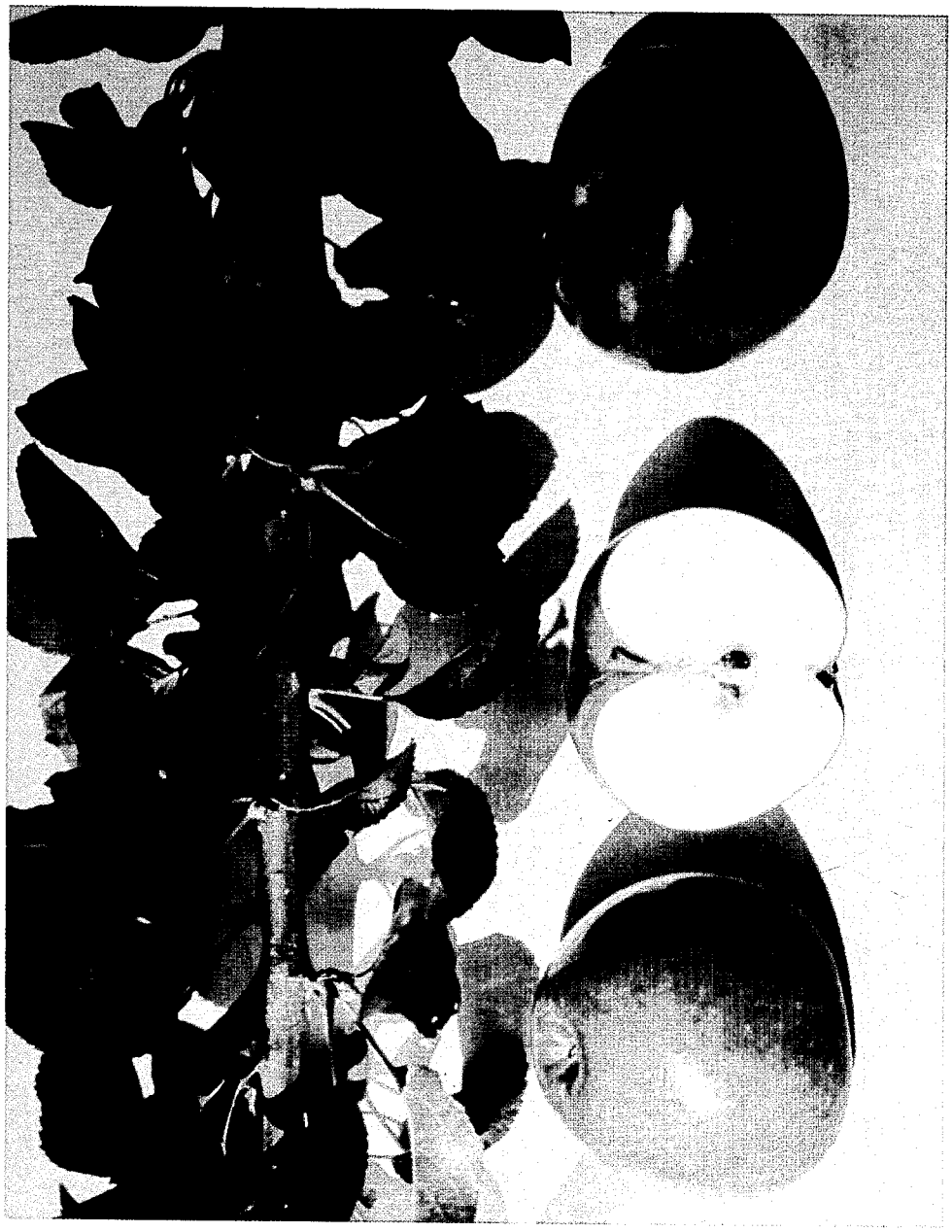
Inventor.
Rudolph M. Mance
By: Robb & Robb
Attorneys.

United States Patent Office

Plant Pat. 2,313
Patented Nov. 19, 1963

2,313
APPLE TREE

Rudolph M. Mance, Naches, Wash., assignor to Stark Bro's. Nurseries & Orchards Company, Louisiana, Mo., a corporation of Missouri

Filed Mar. 19, 1962, Ser. No. 180,912
1 Claim. (Cl. Plt.—34)

The present invention relates to a new and distinct variety of apple tree which was discovered by me as a whole tree bud sport of the well known Winesap variety (unpatented), said discovery having been made in my cultviated orchard which is located near Naches, Washington.

At the time of my discovery, I was growing in my orchard aforesaid apple trees of the standard Winesap variety, and while engaged in routine inspection of the orchard, my attention was attracted to one tree which appeared to have a distinctive spur type of growth that was quite different from the normal habit of the Winesap variety. Closer and prolonged observation of this particular tree aforementioned convinced me that it was a hole tree bud sport of the Winesap variety, and I thereupon promptly took steps to preserve the same and to keep it under close observation.

In due course, I asexually reproduced the new sport by budding, as performed by me in my orchard near Naches, Washington, and the progeny resulting therefrom, together with continued observations and tests of the original sport or mother tree over a period of years, have convinced me and conclusively demonstrated that the sport is definitely a new and distinct variety, as particularly evidenced by the following unique combination of characteristics which are outstanding therein and which distinguish the sport from the standard Winesap variety, as well as from all other varieties of which I am aware:

(1) General similarity of the fruit to that of the variety known as "Stark Red Winesap" (unpatented), also sometimes known as "Virginia Winesap";

(2) A distinctive semi-dwarf tree size, said size being approximately ⅔ the size of "Stark Red Winesap";

(3) A distinctive habit of bearing fruit beginning at an earlier age (about 2 years earlier) than in the case of "Stark Red Winesap";

(4) Greater productivity; and (5) A distinctive and more abundant spur type of growth and development of the fruit.

The accompanying drawing shows typical specimens of the foliage and fruit of my new variety, as well as a typical branch section illustrating the fruiting spur growth, and with one of the fruit specimens shown in cross-section, all as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), Munsell Color Chart (hereinafter abbreviated as "Munsell"), and the Horticultural Colour Guide (hereinafter abbreviated as "HCG"), as indicated, except where general color terms of ordinary dictionary significance are obvious:

Location where grown and observed: Pike County, Missouri, and also State of Washington.

Dates of first and last pickings: About October 12 and about October 18, respectively.

*Tree*

Medium small size; vigorous; spreading; slow-growing; hardy; productive; regular bearer.

Trunk: Medium stocky; smooth.

Branches: Medium thickness; smooth; much-branched.
- *Color.*—Moderate Reddish Brown, Plate 2.5YR 5/5 (Munsell).
- *Lenticels.*—Numerous; medium large.

Leaves: Medium large; medium width; medium short; ovate; taper-pointed; thick; rugose.
- *Average length.*—3½ inches.
- *Average width.*—1 15/16 inches.
- *Color.*—Grayish Olive Green, Plate 2.5GY 3/1 (Munsell).
- *Margin.*—Coarsely serrate.
- *Petiole.*—Medium long; thick. Length—1½ inches.

*Flowers*

Dates of first and full bloom: About May 3 and about May 12, respectively; medium late as compared with other varieties.

Color: Mostly white, with Strong Purplish Pink, Plate 7.5RP 7/10 (Munsell) areas on under (outer) surface.

*Fruit*

Maturity when described: Eating hard ripe.

Size: Uniform.
- *Axial diameter.*—About 2⅜ inches.
- *Transverse diameter.*—About 2¾ inches.

Form: Oblong or slightly conical.

Cavity: Symmetrical; rounded at base; acute; undulate; pubescent toward apex.

Basin:
- *Depth.*—About 9/16 inch.
- *Breadth.*—About 1⅛ inches.
- *Markings.*—Color—Rainette Green, Plate XXXI, Color No. 27″, tone *i* (Ridgway).

Stem: Medium stout; pubescent.
- *Length.*—About 9/16 inch.
- *Breadth.*—About 1/16 inch.
- *Markings.*—Color—Moderate Red, Plate 2.5R 4/10 (Munsell).

Calyx: Closed; segments persistent; acute; about ¼ inch long; approximate; reflexed from base at apex; both outer and inner surfaces pubescent.

Skin: Thick; tough; dull; waxed.
- *Dots.*—Conspicuous; few; small; even; ruptured; circular. Color—Pale Ochraceous Buff, Plate XV, Color No. 15′, tone *f* (Ridgway). Distribution—most numerous in upper middle section.
- *Ground color.*—Primrose Yellow, Plate 601/2, page 65, vol. I (HCG).
- *Color of markings.*—Striped. Color—Delft Rose, Plate 020, page 108, vol. 2 (HCG), overlaid with darker stripes of Currant Red, Plate 821, page 167, vol. 2 (HCG).

Bloom: Wanting.

Scarfskin: Wanting.

General color effect: Dark Red.

Flesh: Rather juicy.
- *Color.*—Dull white, with yellowish tint tinged with red in vascular bundles.
- *Texture.*—Firm; tender; fine.
- *Flavor.*—Subacid.
- *Aroma.*—Wanting.
- *Quality.*—Good.

Core: Distant.
- *Bundle area.*—Small; cordate; symmetrical at base; acute at base.
- *Halves of core.*—Equal.
- *Bundles.*—Inconspicuous. Color—green tinge.
- *Core lines.*—Clasping; indistinct in cross section.
- *Carpellary area.*—Indistinct; small.
- *Calyx tube.*—Pubescent toward base; funnel form;

stem of funnel long. Depth of tube to shoulder—about 3/16 inch. Entire depth—about 9/16 inch.

*Styles.*—Present; distinct toward base; pubescent toward base.

*Stamens.*—In two distinct whorls; median.

*Seed cells.*—Axile; open. Cell walls—thin; tough; length—about 9/16 inch; breadth—about 1/4 inch. Longitudinal section—oval; obtuse at apex. Cross section—broad. Surface—fissured.

Seeds:

*Average number.*—From 6 to 8 perfect; about 2 imperfect; 2 per cell. Length—about 5/16 inch. Breadth—about 3/16 inch.

*Color.*—Moderate Brown, Plate 5YR 3/3 (Munsell).

Use: Market; culinary.

Keeping quality: Good; about 150 days in ordinary storage.

I claim:

A new and distinct variety of apple tree, substantially as herein shown and described, characterized particularly as to novelty by the unique combination of general similarities to the variety "Stark Red Winesap" (unpatented), but being distinguished therefrom by its smaller, semi-dwarf tree size, a distinctive habit of bearing fruit beginning at an earlier age, greater productivity, and a distinctive spur type of growth and development of its fruit.

No references cited.